United States Patent
Ng et al.

(10) Patent No.: US 7,553,505 B2
(45) Date of Patent: Jun. 30, 2009

(54) HEALTH CARE PRODUCT CONTAINING ISOFLAVONE AGLYCONES AND METHOD OF PRODUCING THE SAME

(75) Inventors: Ka Ming Ng, Hong Kong (CN); Qian Luo, Hong Kong (CN); Jingnan Zhang, Hong Kong (CN); Benny Harjo, Kitakyushu (JP)

(73) Assignee: The Hong Kong University of Science and Technology, Hong Kong SAR (CN)

( * ) Notice: Subject to any disclaimer, the term of this patent is extended or adjusted under 35 U.S.C. 154(b) by 0 days.

(21) Appl. No.: 11/622,468

(22) Filed: Jan. 12, 2007

(65) Prior Publication Data

US 2007/0207224 A1    Sep. 6, 2007

Related U.S. Application Data

(60) Provisional application No. 60/758,230, filed on Jan. 12, 2006.

(51) Int. Cl.
*A61K 36/48*    (2006.01)
(52) U.S. Cl. ................................... 424/757
(58) Field of Classification Search ............... None
See application file for complete search history.

(56) References Cited

U.S. PATENT DOCUMENTS

| | | | |
|---|---|---|---|
| 5,670,632 A | 9/1997 | Chaihorsky | |
| 5,858,449 A | 1/1999 | Crank et al. | |
| 6,171,638 B1 | 1/2001 | Gugger et al. | |
| 6,303,161 B1 * | 10/2001 | Takebe et al. | 426/46 |
| 6,369,200 B2 | 4/2002 | Dobbins et al. | |
| 6,410,699 B1 * | 6/2002 | Takebe et al. | 536/8 |
| 6,818,246 B2 | 11/2004 | Singh | |

(Continued)

FOREIGN PATENT DOCUMENTS

CN    1284503 A    2/2001

(Continued)

OTHER PUBLICATIONS

Adlercreutz et al, Urinary excretion of lignans and isoflavonoid phytoestrogens in Japanese men and women consuming a traditional Japanese diet, American Journal of Clinical Nutrition, 1991, vol. 54, pp. 1093-1100.

(Continued)

*Primary Examiner*—Christopher R. Tate
*Assistant Examiner*—Deborah A. Davis
(74) *Attorney, Agent, or Firm*—Eagle IP Limited; Jacqueline C. Lui

(57) ABSTRACT

This invention relates to a novel soy isoflavone product with high purities and strong biological activities and the method of producing the same from natural soybeans, soybean materials (i.e. tofu dregs, soy molasses) and other plant sources. The method includes three steps consisting of extraction with an organic solvent, hydrolysis using an acid and crystallization using an antisolvent. The procedure is very simple and thus can be easily adapted for large-scale manufacturing. Moreover, the procedure is able to produce a high yield of total isoflavones at a lower cost. HPLC analysis and E-Screen bioassay reveal that the obtained product not only contains a high content of isoflavone aglycones by weight of dry matter but also exhibits strong estrogenic activity toward human cells. Therefore, the product should be efficacious for relieving menopausal symptoms and other estrogen-deficient diseases and can be used in health care supplements or as additives for foods, beverages or cosmetics.

17 Claims, 6 Drawing Sheets

U.S. PATENT DOCUMENTS

| | | | | |
|---|---|---|---|---|
| 2002/0122871 | A1* | 9/2002 | Johns et al. | 426/656 |
| 2002/0160064 | A1* | 10/2002 | Zulli et al. | 424/757 |
| 2003/0150805 | A1* | 8/2003 | Collins et al. | 210/634 |
| 2003/0157225 | A1* | 8/2003 | Husband et al. | 426/430 |
| 2005/0123633 | A1* | 6/2005 | Takebe | 424/757 |
| 2006/0052440 | A1* | 3/2006 | Takebe | 514/456 |

FOREIGN PATENT DOCUMENTS

| | | |
|---|---|---|
| CN | 1327983 A | 12/2001 |
| CN | 1449763 A | 10/2003 |
| CN | 1456558 A | 11/2003 |
| CN | 1528758 A | 9/2004 |

OTHER PUBLICATIONS

Adlercreutz et al, Dietary phyto-oestrogens and the menopause in Japan, Lancet, 1992, vol. 339(8803), pp. 233.

Alekel et al, Isoflavone-rich soy protein isolate attenuates bone loss in the lumbar spine of perimenopausal women, American Journal of Clinical Nutrition, 2000, vol. 72, pp. 844-852.

Brzezinski et al, Phytoestrogens: the "natural" selective estrogen receptor modulators?, European Journal of Obstetrics & Gynecology and Reproductive Biology, 1999, vol. 85, pp. 47-51.

Anderson et al, Meta-analysis of the effects of soy protein intake on serum lipids, The New England Journal of Medicine, 1995, vol. 333(5), pp. 276-282.

Sikon et al, Treatment options for menopausal hot flashes, Cleveland Clinic Journal of Medicine, 2004, vol. 71(7), pp. 578-582.

Barnes, Phytoestrogens and breast cancer, Baillière's Clinical Endocrinology and Metabolism, 1998, vol. 12(4), pp. 559-579.

Brandi, Phytoestrogens and menopause, Environmental Toxicology and Pharmacology, 1999, vol. 7, pp. 213-216.

Choi et al, p53-independent Induction of p21(WAF1/CIP1), Reduction of Cyclin B1 and G2/M Arrest by the Isoflavone Genistein in Human Prostate Carcinoma Cells, Japanese Journal of Cancer Research, 2000, vol. 91, pp. 164-173.

Clarkson et al, Estrogenic Soybean Isoflavones and Chronic Disease—Risks and Benefits, Trends in Endocrinology and Metabolism, 1995, vol. 6(1), pp. 11-16.

Cornwell et al, Dietary phytoestrogens and health, Phytochemistry, 2004, vol. 65, pp. 995-1016.

Dixon et al, Molecules of Interest: Genistein, Phytochemistry, 2002, vol. 60, pp. 205-211.

Ettinger et al, Effect of the Women's Health Initiative on Women's Decisions to Discontinue Postmenopausal Hormone Therapy, Obstetrics & Gynecology, 2003, vol. 102(6), pp. 1225-1232.

Ingram et al, Case-control study of phyto-oestrogens and breast cancer, Lancet, 1997, vol. 350, pp. 990-994.

Izumi et al, Soy Isoflavone Aglycones Are Absorbed Faster and in Higher Amounts than Their Glucosides in Humans, Journal of Nutrition, 2000, vol. 130, pp. 1695-1699.

King et al, Concentrations of isoflavone phytoestrogens and their glucosides in Australian soya beans and soya foods, Australian Journal of Nutrition and Dietetics, 2000, vol. 57(2), pp. 70-78.

Knight et al, A Review of the Clinical Effects of Phytoestrogens, Obstetrics & Gynecology, 1996, vol. 87(5), pp. 897-904.

Lamartiniere et al, Neonatal Genistein Chemoprevents Mammary Cancer, Proceedings of the Society for Experimental Biology and Medicine, 1995, vol. 208, pp. 120-123.

Lawton et al, Changes in use of hormone replacement therapy after the report from the Women's Health Initiative: cross sectional survey of users, British Medical Journal, 2003, vol. 327, pp. 845,846.

Lee at al, Dietary effects on breast-cancer risk in Singapore, Lancet, 1991, vol. 337, pp. 1197-1200.

Lee et al, Alternative Therapies Used by Women With Breast Cancer in Four Ethnic Populations, Journal of the National Cancer Institute, 2000, vol. 92(1), pp. 42-47.

Lindsay, Hormone replacement therapy and osteoporosis, The Prescriber's Guide to Hormone Replacement Therapy, 1998, pp. 19-23, Parthenon Publishing Group.

Messina et al, The Role of Soy Products in Reducing Risk of Cancer, Journal of the National Cancer Institute, 1991, vol. 83(8), pp. 541-546.

Murphy et al, Isoflavones in Retail and Institutional Soy Foods, Journal of Agricultural and Food Chemistry, 1999, vol. 47(7), pp. 2697-2704.

Naim et al, Soybean isoflavones. Characterization, Determination, and Antifungal Activity, 1974, vol. 22(5), pp. 806-810.

Peñnalvo et al, A simplified HPLC method for total isoflavones in soy products, Food Chemistry, 2004, vol. 87, pp. 297-305.

Piskula et al, Daidzein and genistein but not their glucosides are absorbed from the rat stomach, FEBS Letters, 1999, vol. 447, pp. 287-291.

Apers et al, Fast high-performance liquid chromatography method for quality control of soy extracts, Journal of Chromatography A, 2004, vol. 1038, pp. 107-112.

Setchell et al, Bioavailability of Pure Isoflavones in Healthy Humans and Analysis of Commercial Soy Isoflavone Supplements, Journal of Nutrition, 2001, vol. 131, pp. 1362S-1375S.

Setchell et al, Evidence for lack of absorption of soy isoflavone glycosides in humans, supporting the crucial role of intestinal metabolism for bioavailability, American Journal of Clinical Nutrition, 2002, vol. 76, pp. 447-453.

Setchehll et al, Comparing the pharmacokinetics of daidzein and genistein with the use of 13C-labeled tracers in premenopausal women, American Journal of Clinical Nutrition, 2003, vol. 77, pp. 411-419.

Severson et al, A Prospective Study of Demographics, Diet, and Prostate Cancer among Men of Japanese Ancestry in Hawaii, Cancer Research, 1989, vol. 49, pp. 1857-1860.

Dantas, Menopausal Symptoms and Alternative Medicine, Primary Care Update for OB/GYNS, 1999, vol. 6(6), pp. 212-220.

Stopper et al, Genotoxicity of phytoestrogens, Mutation Research, 2005, vol. 574, pp. 139-155.

Strauss et al, Dietary phytoestrogens and their role in hormonally dependent disease, Toxicology Letters, 1998, vol. 102-103, pp. 349-354.

Wang et al, Isoflavone Content in Commerical Soybean Foods, Journal of Agricultural and Food Chemistry, 1994, vol. 42(8), pp. 1666-1673.

Wang et al, Isoflavone Composition of American and Japanese Soybeans in Iowa: Effects of Variety, Crop Year, and Location, Journal of Agricultural and Food Chemistry, 1994, vol. 42(8), pp. 1674-1677.

Wang et al, Mass Balance Study of Isoflavones during Soybean Processing, Journal of Agricultural and Food Chemistry, 1996, vol. 44(8), pp. 2377-2383.

Watanabe et al, Colon Cancer: An Approach from Molecular Epidemiology, Journal of Epidemiology, 1993, vol. 3(2), pp. 47-61.

Rossouw et al, Risks and Benefits of Estrogen Plus Progestin in Healthy Postmenopausal Women: Principal Results From the Women's Health Initiative Randomized Controlled Trial, Journal of the American Medical Association, 2002, vol. 288(3), pp. 321-333.

* cited by examiner

HEALTH CARE PRODUCT CONTAINING ISOFLAVONE AGLYCONES AND METHOD OF PRODUCING THE SAME

CROSS-REFERENCE TO RELATED APPLICATIONS

This application claims the benefit of provisional application Ser. No. 60/758,230 filed on 12 Jan. 2006, under 35 U.S.C. §119(e) (specifically incorporated herein by reference in its entirety)

FIELD OF INVENTION

This invention relates generally to isoflavones, and more particularly to a method of producing isoflavones with high purities and strong biological activities from natural soybeans, soybean materials (i.e. tofu dregs, soy molasses) and other plant sources.

BACKGROUND OF INVENTION

Recently, interest in soy isoflavones has increased around the world because epidemiologic studies have shown that the consumption of soy isoflavones may be associated with both low incidence rates of certain cancers, such as breast cancer, prostate cancer, uterine cancer, colon cancer, etc., and reduction in the risk of various diseases including cardiovascular problems, osteoporosis and menopausal symptoms. In 1996, Food and Drug Administration of the USA approved selling soy isoflavones as health food or supplement on the market. At present, the soy isoflavone products are popular in Europe and the USA.

Isoflavones are a flavanoid subgroup found in a variety of plants, with significantly high amounts in soybeans. Natural soybeans contain 1.2-4.2 mg of total isoflavones /g of sample, with large variation due to variety, crop year and growth location, whereas the content in soybean products (i.e. tofu, miso, soy protein, soy milk) generally does not exceed 0.2% dry weight. To date, twelve main isoflavones (Table 1, Rostagno et al., 2004, *Analytica Chimica Acta*, 522: 169-177) have been characterized in soybeans and soybean products including genistein, daidzein and glycitein and their respective malonyl, acetyl and glucosyl forms. The three families of genistein, daidzein and glycitein are found in an approximate ratio of 6:3:1. It should be noted that most of isoflavones are present in the form of glucosides in natural soybeans and non-fermented soy products (soy protein, soy milk, etc.), with genistin and daidzin accounting for the major portion, and only 2 to 5% of isoflavones are aglycones, but the physiological effects of soy products are mainly contributed by their aglycones.

TABLE 1

Aglycones:

| Compounds | Symbol | R₁ | R₂ |
|---|---|---|---|
| Daidzein | De | H | H |
| Glycitein | Gle | H | OCH₃ |
| Genistein | Ge | OH | H |

TABLE 1-continued

Glucosides:

| Compounds | R₁ | R₂ | R₃ |
|---|---|---|---|
| Daidzin | Di | H | H | H |
| Glycitin | Gly | H | OCH₃ | H |
| Genistin | Gi | OH | H | H |
| Acetyldaidzin | AcDi | H | H | COCH₃ |
| Acetylglycitin | AcGly | H | OCH₃ | COCH₃ |
| Acetylgenistin | AcGi | OH | H | COCH₃ |
| Malonyldaidzin | MDi | H | H | COCH₂COOH |
| Malonylglycitin | MGly | H | OCH₃ | COCH₂COOH |
| Malonylgenistin | MGi | OH | H | COCH₂COOH |

Soy isoflavones have been reported to have a variety of biological activities. Due to the estrogenic activity of isoflavones, nowadays they are used instead of traditional hormone replacement therapy (HRT) for treating estrogen-deficient women in menopause or postmenopause.

One better alternative is soy isoflavones. Since isoflavones structurally resemble genuine 17β-estradiol ($E_2$) and have weak estrogenic activities, they can mimic or modulate the actions of endogenous estrogens in vertebrates by binding to estrogen receptors (ERs). For example, genistein shares structural features with the potent estrogen $E_2$, so it can exert estrogenic activity.

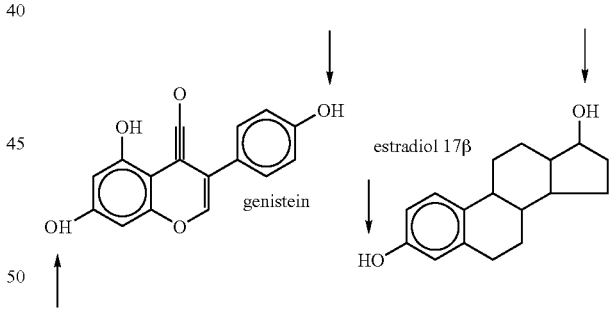

Structure of an isoflavone (genistein) is relative to that of endogenous estrogen (17β-estradiol).

Many problems have been found in the processes for manufacturing soy isoflavones. Firstly, repeated extraction with organic solvents or separation by chromatography was used to purify soy isoflavones in most prior art techniques. But these two methods are not only costly but also too complicated to be applied for a large-scale production. Secondly, toxic organic solvents including acetone, ether, hexane, chloroform, etc. were extensively used. But the remains of these toxic solvents in the products will likely endanger human health when these products are used for making drugs, foods, cosmetics, etc.

SUMMARY OF INVENTION

In the light of the foregoing background, it is an object of the present invention to provide a simple and low-cost method to manufacture a health care product containing a high content of isoflavone aglycones.

Accordingly, the present invention, in one aspect, is a health care product comprising isoflavone aglycones including genistein, daidzein and glycitein, with genistein and daidzein in the weight ratio of 4:1 to 1:4.

In a preferred embodiment of the present invention, the health care product does not contain any toxic solvents with ethanol being used as the solvent for extraction.

In another preferred embodiment of the present invention, the health care product has strong biological activities especially directed to specific health problems including menopausal symptoms and other estrogen-deficient diseases.

According to another aspect of the present invention, a method is provided for manufacturing the health care product from starting materials containing isoflavones which comprises grinding the starting materials into small particles preferably to obtain flour, extracting the flour with an organic solvent to recover isoflavones, hydrolyzing the extract to convert isoflavone glucosides into aglycones, and crystallizing the aglycones with an antisolvent. The resulting aglycone fractions are then collected or further purified.

In a preferred embodiment of the present invention, the starting materials used for manufacturing the health care product include natural soybeans, soybean materials (including tofu dregs, soy molasses, soy grits, etc., and mixtures thereof), lentil, chickpea, split pea, broad bean, kudzu, alfalfa, red clover, subterranean clover, etc., and mixtures thereof. In the most preferred embodiment, natural soybeans or soybean materials are used as the starting materials.

In another preferred embodiment, the solvent used for extraction includes ethanol, methanol, acetone and other organic solvents. In the most preferred embodiment, ethanol is used to ensure the health care product will not endanger human health even with the remains of solvent. The acid used for hydrolysis includes hydrochloric acid, acetic acid and other acids. In the most preferred embodiment, hydrochloric acid or acetic acid is used. And the antisolvent used in the crystallization step is water.

In one implementation of the above method, the starting materials are ground into small particles preferably to obtain flour before extraction.

In another implementation of the above method, the extraction step further comprises mixing the flour with an organic solvent, heating the resulting mixture and filtrating the mixture to remove undissolved particles and obtain an extract of isoflavones. Further, the hydrolysis step is performed using the extract (filtrate).

In still another implementation of the above method, the hydrolysis step further comprises mixing the extract with an acid and heating the resulting mixture. This process of hydrolysis almost converts all the isoflavone glucoside fractions into aglycones, improving the efficacy and absorbability of the isoflavone products.

In yet another implementation of the above method, the crystallization step further is composed of mixing the hydrolyzed extract with an antisolvent, cooling the resulting mixture, filtrating the mixture to obtain isoflavone aglycone crystals and drying the isoflavone crystals to form a product.

There are many advantages resulting from crystallization and the following filtration. Firstly, simple processes of crystallization and filtration are used instead of the complicated ones such as repeated extraction, chromatography and centrifugation which have been commonly used in the approved patents of manufacturing isoflavones. Therefore, this invention can be easily adapted for large-scale manufacturing. Secondly, crystallization and filtration not only avoid the usage of expensive chromatography column and centrifuge but also significantly reduce the energy consumption for evaporating the liquid fractions. Therefore, the cost of this invention is greatly reduced. Thirdly, crystallization achieves a high yield of total isoflavones and the obtained product contains a high content of isoflavone aglycones.

In another preferred implementation of the above method, additional steps of washing the isoflavone aglycone crystals with a solvent, re-dissolving the washed product in a solvent, concentrating the re-dissolved product and re-crystallizing it with an antisolvent to form second crystals, and drying the second crystals to form the final product are provided.

Apart from the final product, the above method also results in an intermediate product that can be conveniently stored for later processing into a more pure form of isoflavone combination or into the form of isoflavone aglycone single compound by separation.

According to a still further aspect of the invention, the product of crystallization is measured isoflavone content by HPLC and assessed estrogenic activity by E-Screen bioassay. As a result, the product thus obtained contains a mixture of isoflavone aglycones with high purities (in an example, the content of total aglycones exceeds 10% for primary product and 60% after further purifications by weight of the dry matter) and exerts strong estrogenic activity toward human cells. Then, the product can be used as a health care supplement for relieving menopausal symptoms of women and other estrogen-deficient diseases such as osteoporosis and cardiovascular problems. Besides, the product can also be used as a supplement which may be included in a great variety of foods, beverages and cosmetics and to be of benefit to human health especially to menopausal and postmenopausal women.

DETAILED DESCRIPTION OF THE PREFERRED EMBODIMENTS

Figure 1:
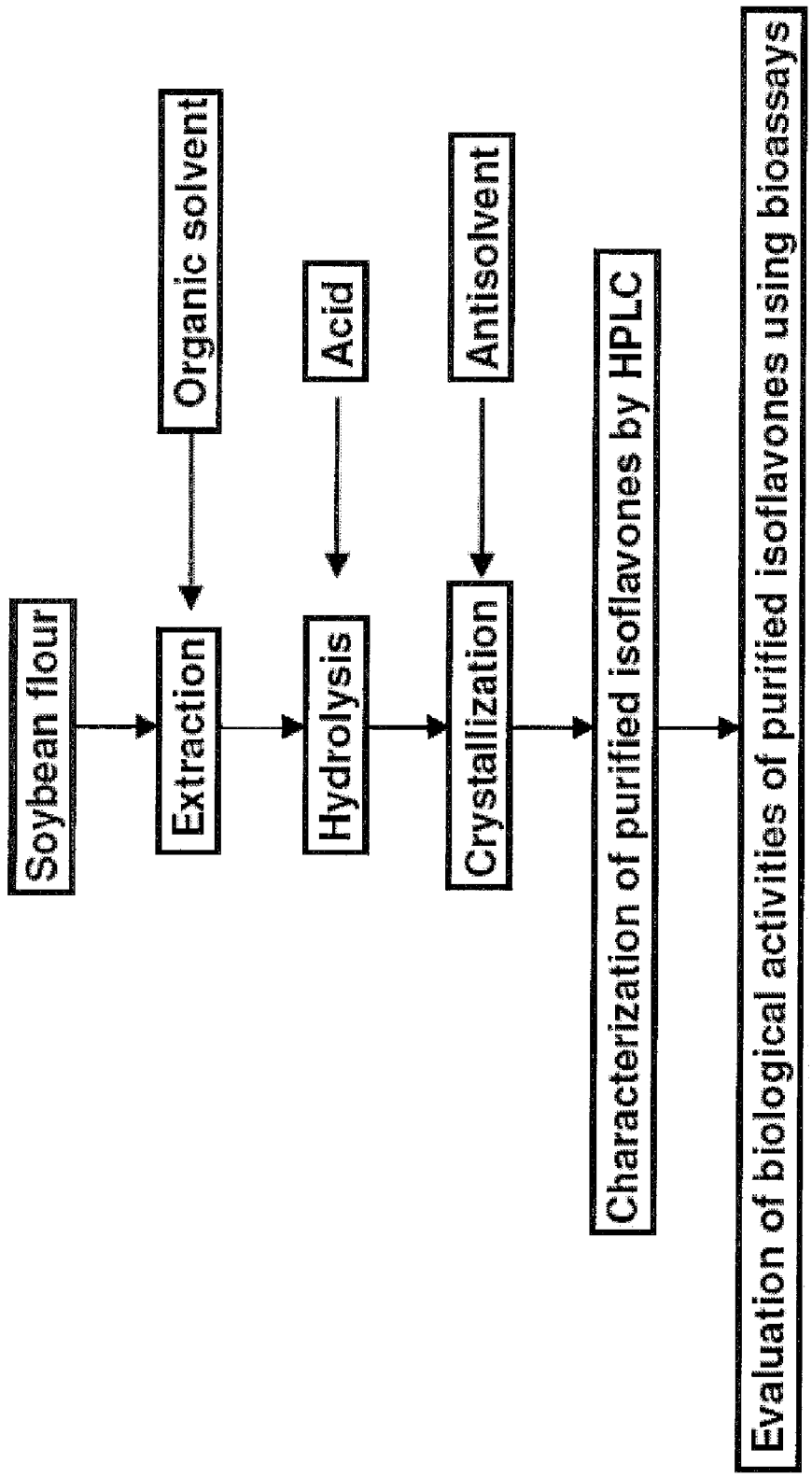
FIG. 1 is a process flow diagram of the method of extracting and purifying isoflavones from soybeans according to one embodiment of the present invention.

Referring now to FIG. 1, the first embodiment of the present invention is the method of extracting and purifying isoflavones mainly encompassing three steps: 1) extracting isoflavones from starting materials such as soybean flour with an organic solvent; 2) hydrolyzing the isoflavone glucoside fractions of the extract into aglycones using an acid; 3) crystallizing the aglycones by addition of antisolvent to the product of hydrolysis.

The invention begins with starting materials containing isoflavones. Such materials include, but are not limited to, natural soybeans, soybean materials (including tofu dregs, soy molasses, soy grits, etc., and mixtures thereof), lentil, chickpea, split pea, broad bean, kudzu, alfalfa, red clover, subterranean clover, etc., and mixtures thereof. In the most preferred embodiment, natural soybeans or soybean materials are used. These soybean materials are often generated as by-products of many commercial processes, such as the processes for producing tofu and soy protein concentrates. Accordingly, many soybean materials are produced in large quantities and they are inexpensive and commercially available commodity.

Figure 2:
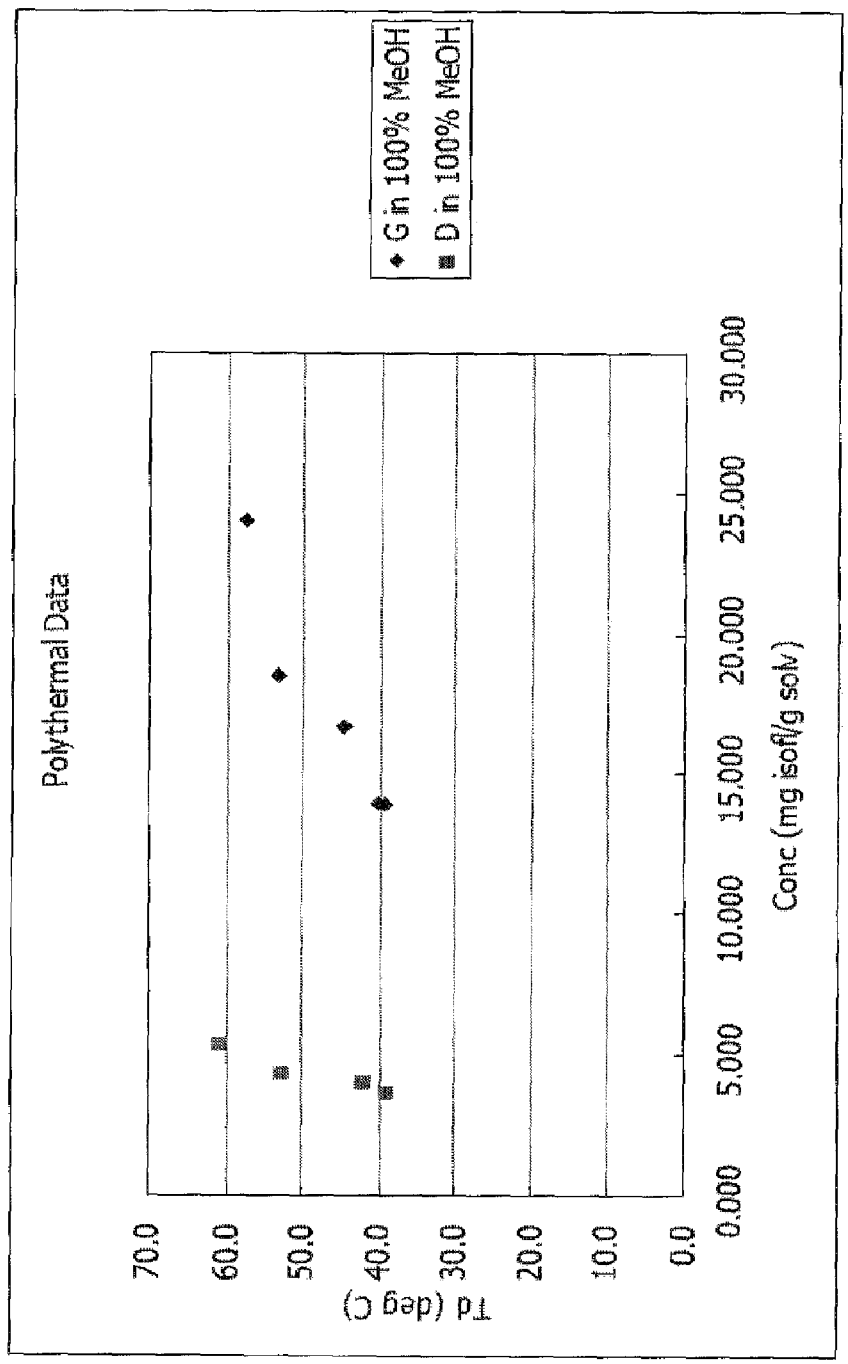
FIG. 2 is a diagram showing the solubilities of genistein and daidzein in methanol against temperature.

The first step of the method as described above is extraction. This process of grinding starting materials disrupts their tissue structure to enable the isoflavone fractions more easily extracted by the organic solvent. Then, an organic solvent, preferably ethanol, is used to recover isoflavones based on the high solubilities and steadiness of isoflavones in the selected solvents. Notably, the solubilities of some isoflavones (i.e. genistein) in alcohol including methanol and ethanol increase evidently with increasing temperature within the specific range as illustrated in FIG. 2. Ethanol (edible alcohol) is preferred in this invention to ensure the isoflavone product will not endanger human health even with the remains of solvent. The extraction is carried out at a temperature ranging from 40 to 90° C. for 2-24 hrs, with the material ratio (volume:weight) of solvent to flour between 1:1 and 10:1 (mL:g).

The second step described above is hydrolysis, whose purpose is to convert the isoflavone glucosides into aglycones in order to improve the efficacy and absorbability of the resulting isoflavone products. For hydrolysis, the extract is mixed with an acid preferably 37% hydrochloric acid or pure acetic acid such that the pH of the resulting mixture is adjusted to be within the range of 1 to 5. The mixture is then heated to a temperature between 40-90° C. for 1-12 hrs such that almost all of the glucoside fractions of extract are transformed into aglycones.

The third step described above is crystallization. The process of crystallization is based on the different solubilities of isoflavone aglycones in different solvents. An antisolvent is defined as a poor solvent wherein the solute will have relatively low solubility. So upon addition of the antisolvent, the solubilities of isoflavone aglycones decrease rapidly. Therefore, the isoflavone aglycones will crystallize from the solution and the resulting crystals can be separated from the liquid fractions by simple filtration. In the most preferred embodiment of the invention, water is used as the antisolvent due to the much lower solubilities of isoflavone aglycones in water than in alcohol and the vast availability of water. Further, since most co-extracted impurities are water-soluble, the use of water as antisolvent helps to separate these impurities from the crystals of isoflavone aglycones. For crystallization, the hydrolyzed extract is mixed with water at the volume ratio of 1:1 to 15:1 (mL:mL). In addition, to enhance the crystal yields of some isoflavones such as genistein, the mixture is cooled to room temperature or below for at least 10 min. Then the isoflavone aglycone crystals are dried to obtain a product wherein drying can further remove the impurities (mainly solvents).

Apart from the steps as listed in FIG. 1, additional steps of washing the isoflavone aglycone crystals with a solvent, re-dissolving the washed product in the solvent, concentrating the re-dissolved product, and re-crystallizing the concentrated product with an antisolvent may be implemented and even repeated to increase the purities of isoflavones and further remove the impurities from the product. Besides, upon further purifications, the product with more than 60% dry weight of isoflavone aglycones and few impurities can be obtained.

The product of the invention is a mixture of genistein, daidzein, glycitein and few impurities. Highly-purified isoflavone single compounds can be separated from the product easily based on re-crystallization. Since the product may be held in solid form, it will be convenient for storage, shipping and usage as drugs in various formulas and as additives of food, beverages or cosmetic products.

There are many advantages to the present invention. First of all, in this invention, complicated and expensive steps (repeated extraction, chromatography and centrifugation) which have been commonly used in the prior art related to the production of isoflavones were replaced with simple and low-cost steps (crystallization and filtration). Therefore, this invention can be easily adapted for large-scale manufacturing that requires lower cost and less equipment to achieve a high yield of more consistently pure isoflavone product, especially a product containing a high content of isoflavone aglycones.

Besides the simplicity and low cost, the advantages of this invention also include:

(1) High efficiency: This simple procedure is very effective and able to produce a high yield of total isoflavones (about 0.6 mg/g sample for Sigma-Aldrich soybean flour). In considering that natural soybeans only contain 1.2-4.2 mg/g of total isoflavones, the yield of this invention is higher than the prior art results. Many batches of extraction and purification have been performed and the batch-to-batch variation of the yield of total isoflavones does not exceed 20% using the same starting materials.

(2) Safe and efficacious product: Ethanol (edible alcohol) is preferred in this invention as the solvent for extraction to ensure the product will not endanger human health even if trace amount of the solvent remains. They are also more environmentally friendly to be disposed of or may be recycled. In addition, acid is used to almost completely convert isoflavone glucosides into the corresponding aglycones to improve the efficacy and absorbability of the product.

The present invention is further defined by the following examples, which are not intended to limit the present invention.

EXAMPLE 1

Preferred Method for Extracting and Purifying Isoflavones

Isoflavones were extracted and purified in the following steps:

1. 160 g of dry soybean flour (Sigma-Aldrich, USA) was mixed with 480 mL of 95% ethanol. The mixture was heated to about 80° C. with stirring and then incubated in a 80° C. water bath for 8 hrs.
2. Afterwards, the solid residue was removed by filtration through No. 1 filter paper (Whatman, UK) and about 250 mL of extract was obtained.
3. For hydrolysis, the extract was mixed with 4 mL of 37% hydrochloric acid. The mixture was heated to about 80° C. with stirring and then incubated in a 80° C. water bath for 6 hrs.
4. The hydrolyzed extract was cooled to room temperature and mixed with 1000 mL of water with stirring to promote crystal formation of isoflavones.

5. The resulting isoflavone crystals were separated from the liquid solution by filtration through 0.20 μm membranes (Millipore, USA) and the collected crystals were dried to form the product.

Evaluation of Product

In order to measure the content of isoflavones and evaluate the estrogenic activity, the dried product was completely dissolved in 60 mL of pure ethanol and this solution was respectively used for HPLC (high pressure liquid chromatography) analysis and E-Screen bioassay.

Content of Isoflavones

The sample was filtered through 0.20 μm syringe filter (Millex, Japan) before HPLC analysis. The HPLC analysis was performed using a reversed-phase $C_{18}$ column (Phenomenex, 5 μm, 250×4.6 mm i.d.) on the Agilent 1100 Series liquid chromatograph (including the pumping system, vacuum degasser, auto-sampler, and UV-DAD detector). The sample injection volume was 10 μL. The mobile phase was water with 0.1% acetic acid (A) and methanol (B). A linear gradient elution was applied from 30% B to 50% B starting from 0 minute to 45 minute, at a flow rate of 1.0 mL/min. The column temperature was maintained at 40° C. using a thermostat. UV spectra were detected at the wavelength of 255 nm where absorbance peak areas were quantified.

Figure 3A:
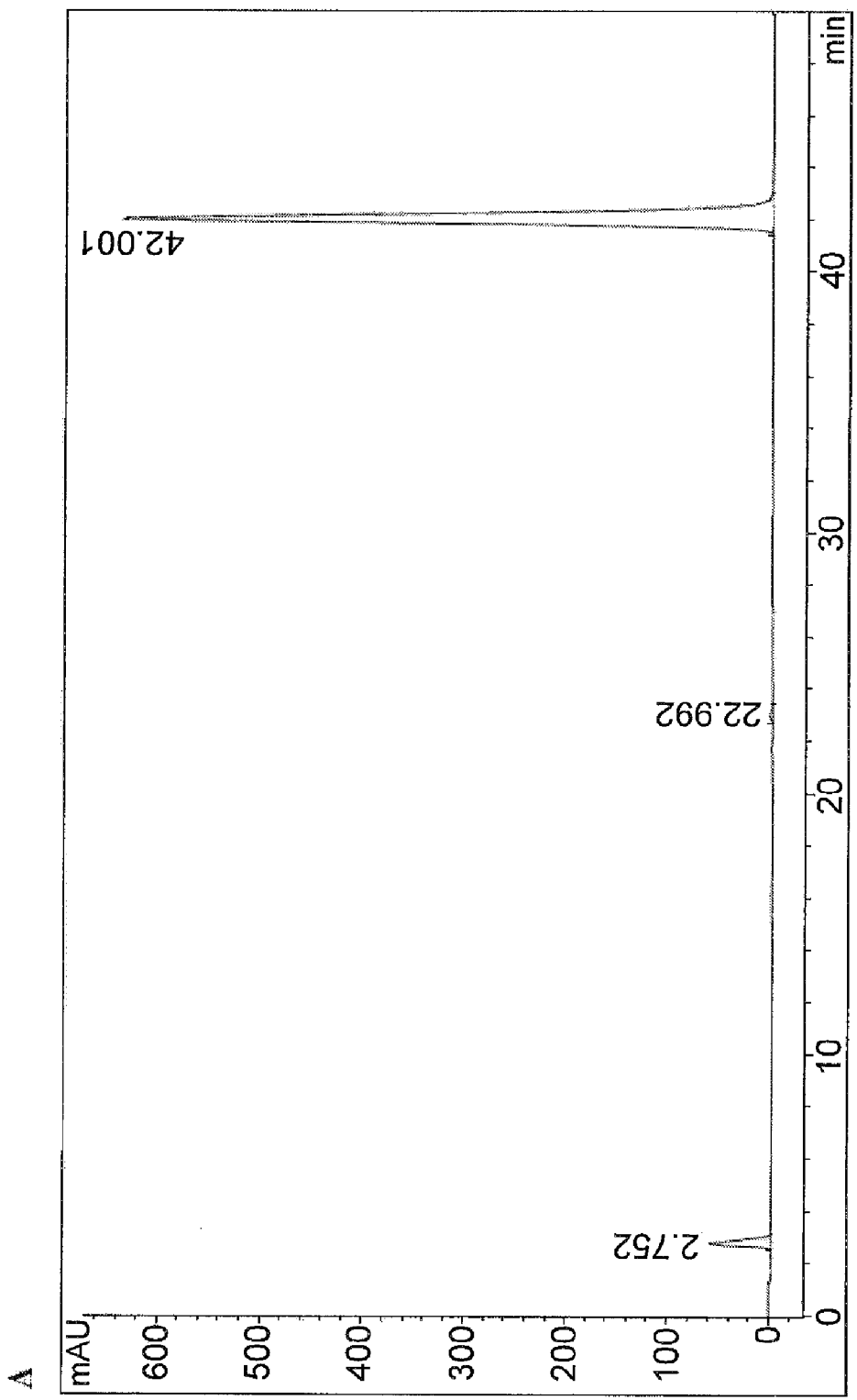
FIG. 3 is a HPLC chromatogram of pure genistein (A) and pure daidzein (B) (soy aglycone standards from LC Labs, USA).
Figure 3B:
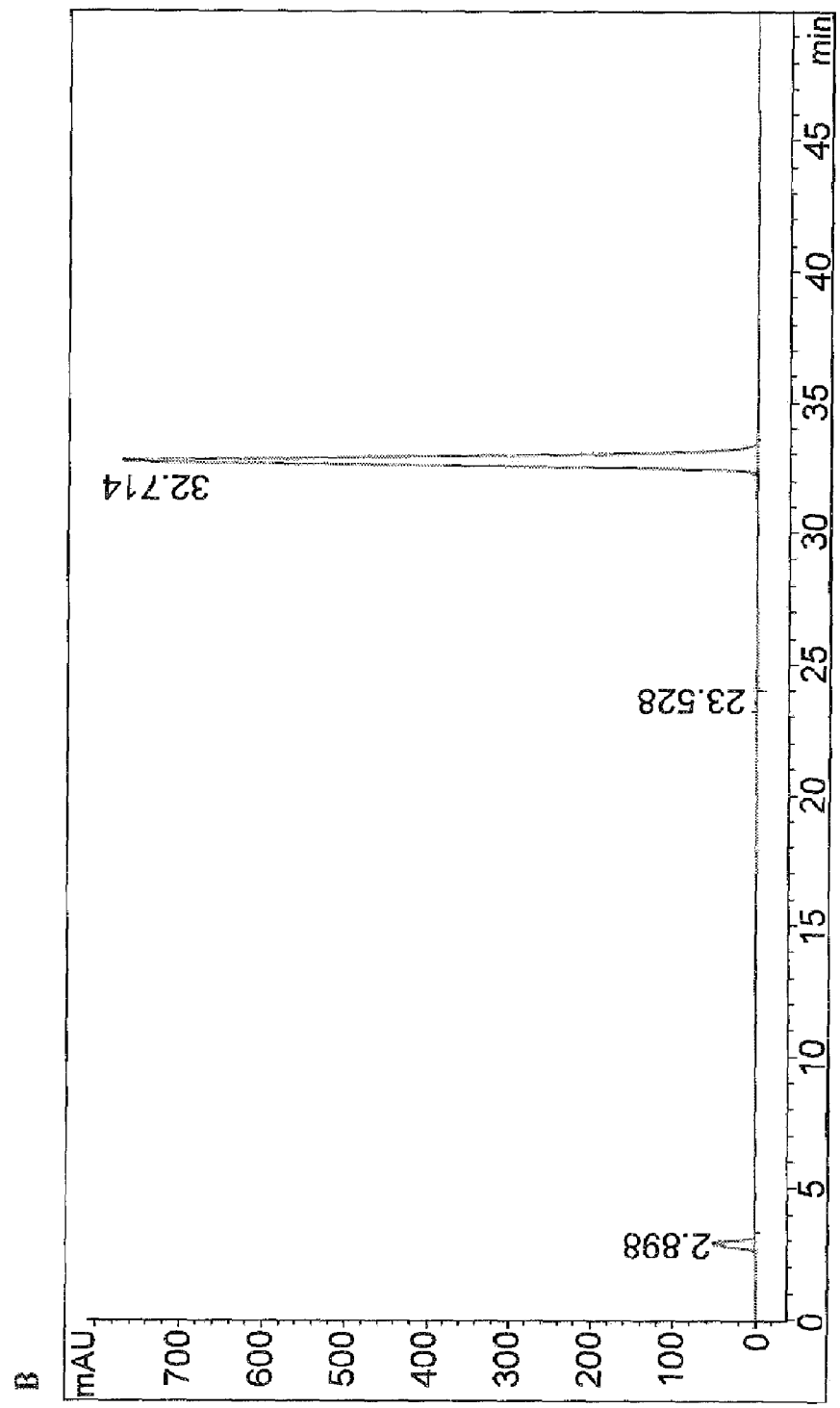

The identification of each isoflavone was made by comparison of retention times with those of pure isoflavone standards (FIG. 3), as well as by UV spectra comparison. Quantitative analysis was done by using calibration curves. Isoflavone standards, daidzein, genistein and glycitein with purity higher than 99% (LC Labs, USA), were prepared in serial concentrations, and then the curves were constructed: $Y=75.67208\ x-33.71133$ for genistein, $R^2=0.99991$; $Y=51.05030\ x+82.10938$ for daidzein, $R^2=0.99989$. The correlation coefficient of each curve reached 0.999.

Figure 4:
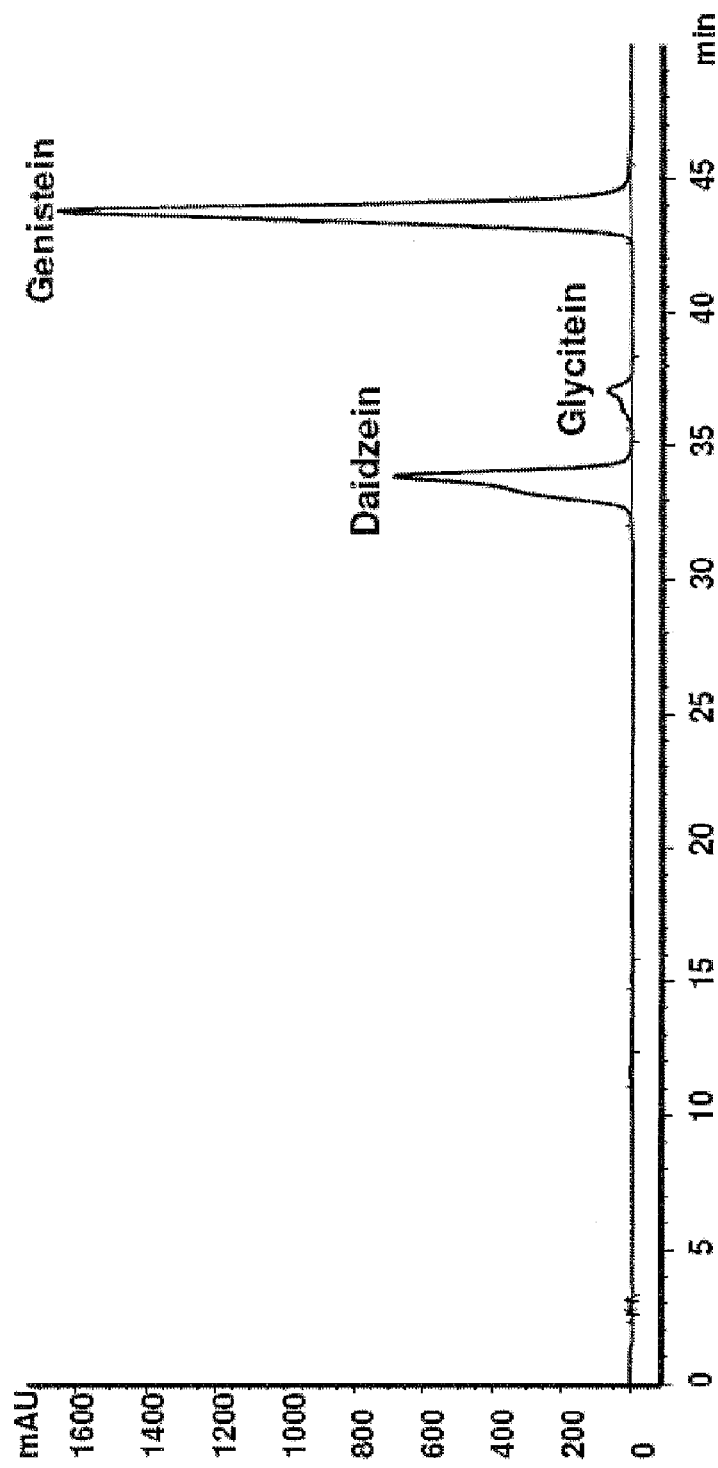
FIG. 4 is a HPLC chromatogram of the dried product of Example 1 which contains a high content of isoflavone aglycones (including genistein, daidzein and glycitein).

HPLC chromatogram of isoflavone aglycones (genistein, daidzein and glycitein) in the product of Example 1 was shown in FIG. 4. By applying the corresponding regression parameters, the level of each aglycone in this product was deduced: 0.942 mg/mL for genistein and 0.641 mg/mL for daidzein. Genistein and daidzein were the main isoflavone components, with genistein occupying about 60% of total isoflavones and daidzein occupying about 40%, and few impurities were included in the product. Then the content of isoflavone aglycones in the dried product was calculated to be about 10% of the total dry weight.

Estrogenic Activity

The estrogenic activity of the product was assessed by E-SCREEN bioassay using cultured human MCF-7 cells. In this assay, the estrogenic activities of the test samples were measured quantitatively by assaying the proliferation of MCF-7 cells (estrogen-sensitive cell line) (Soto et al., 1995, *Environ. Health Perspect.,* 103 (suppl. 7): 113-122). This assay compares the cell number of human MCF-7 cells in the absence of estrogens (negative control) and in the presence of 17β-estradiol (positive control) or estrogenic compounds. This bioassay has been suggested to be a sensitive and reliable tool to assess the ER-mediated estrogenic activity.

Cell number was determined by the MTT [3-(4,5-dimethylthiazol-2-yl)-2,5-diphenyltetrazolium bromide] assay. The initial cell number was determined to be $4-5\times10^3$ cells/well to keep an almost linear correlation between the number of cells and the OD (optical density) values during the incubation period. After maintenance in the standard culture medium (phenol red-free medium with charcoal-stripped serum) for more than four days, MCF-7 cells were seeded into 96-well plate with 100 μL cell solution (about $5\times10^4$ cells/mL) per well. Cells were allowed to attach to the bottom of the 96-well plate after 24 hours of incubation. At $t_0$ the old medium was replaced by the new standard medium containing different test samples. In the experiments, MCF-7 cell yields were measured every 24 hours until 5 days after $t_0$. At each time point (Day 0, Day 1, . . . ) an aliquot (10 μL) of the MTT labeling solution was added into each well, and the mixture was incubated in the dark for 4 hours under regular growth conditions. Then 100 μL of solubilization solution was added into each well, and the mixture was incubated under regular growth conditions for 20 hours. Then the OD of each well was measured at the wavelength of 595 nm using an absorbance microplate reader (Bio-Rad, USA). Each MTT assay included blank controls containing standard medium (without cells) and the test samples, and the net absorbance value was obtained after subtracting the average value of the blank from the test value. The corrected absorbance value represents a reliable estimate of the proliferation effects of the test samples.

Figure 5:
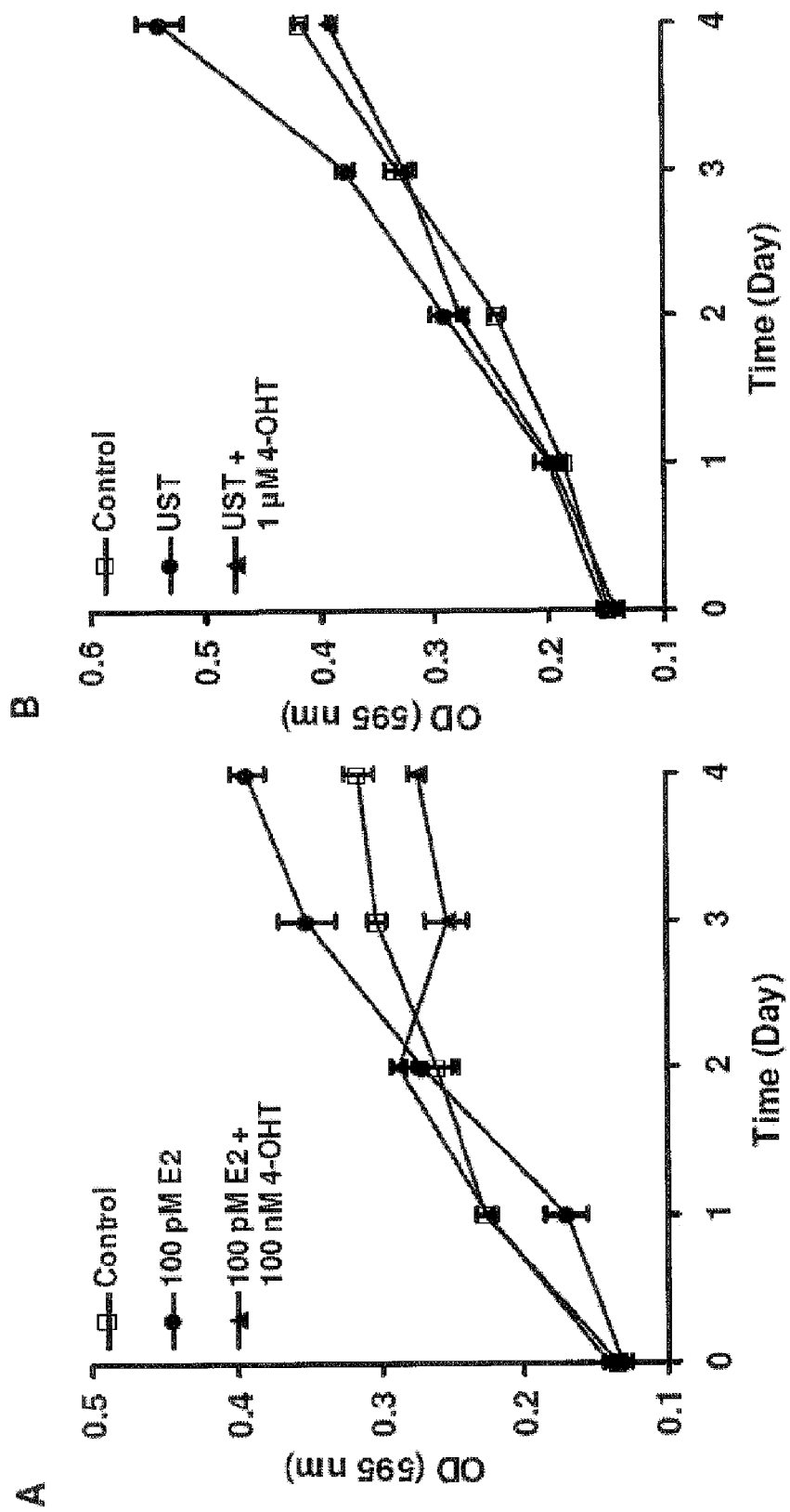
FIG. 5 is a diagram showing the MTT results which reflect MCF-7 cell proliferation induced respectively by endogenous level of 17β-estradiol (A) and by the product of Example 1 at the concentration of 0.4 μg total isoflavones/mL (B).

According to the MTT results as illustrated in FIG. 5, the product exerted a strong ER-dependent estrogenic activity toward the human cells (FIG. 5B) and its activity was similar with the one (FIG. 5A) of endogenous level of 17β-estradiol.

Conclusion

The specific features of the soy isoflavone product generated by this invention are summarized as the following. First of all, HPLC analysis revealed that the product contained a high content of isoflavone aglycones and only few impurities. Moreover, the major isoflavone component in the product was genistein. Since genistein has the highest biological activities among the twelve soy isoflavones (Mitchell et al., 1998, *Arch Biochem Biophys,* 360: 142-148; Setchell et al., 2003, *J Agric Food Chem,* 51(14): 4146-4155), the product should have strong biological activity. Then E-Screen bioassay identified that the product had a strong estrogenic activity and could mimic the effect of endogenous level of $E_2$ on human cells. Therefore, the product will be efficacious for relieving menopausal symptoms and other estrogen-deficient diseases. Thus the objective of the invention has been met.

The preferred embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, although the most preferred embodiment describes the use of ethanol or edible alcohol as the extracting solvent, methanol and acetone can be used in another embodiment of the present invention. A person skilled in the art will appreciate that other solvents may be used, such as acetic acid, anisole, 1-butanol, 2-butanol, cumene, dimethylsulfoxide, ethyl acetate, ethyl ether, ethyl formate, formic acid, heptane, isobutyl acetate, isopropyl acetate, methyl acetate, 3-methyl-1-butanol, methyl-t-butyl ether, methyl ethyl ketone, 1-pentanol, 1-propanol, and tetrahydrofuran.

A person skilled in the art will also appreciate that although water is used as the antisolvent in the precipitation to crystallize isoflavone aglycone, other antisolvents may be used, such as acetic acid, acetone, anisole, 1-butanol, 2-butanol, cumene, dimethylsulfoxide, ethanol, ethyl acetate, ethyl ether, ethyl formate, formic acid, heptane, isobutyl acetate, isopropyl acetate, methyl acetate, 3-methyl-1-butanol, methyl-t-butyl ether, methyl ethyl ketone, 1-pentanol, 1-propanol, and tetrahydrofuran.

What is claimed is:

1. A method of extracting and purifying isoflavone aglycones comprising the steps of:
   a. choosing starting materials that comprise isoflavones;
   b. grinding said starting materials in step (a) into small particles to obtain a flour;
   c. extracting said flour obtained in step (b) with an organic solvent having a concentration of 95% to 99.99% to produce an organic solvent extract of isoflavones;
   d. hydrolyzing said organic solvent extract obtained in step (c) with acid to convert isoflavone glucosides into isoflavone aglycones to produce a hydrolysate; and
   e. adding water into said hydrolysate obtained in step (d) to increase the volume thereof to form an aqueous mixture and crystallizing said isoflavone aglycones from said aqueous mixture.

2. The method according to claim 1, wherein said starting materials in step (a) are selected from the group consisting of natural soybeans, soybean materials, lentil, chickpea, split pea, broad bean, kudzu, alfalfa, red clover, subterranean clover, and mixtures thereof.

3. The method according to claim 1, wherein said organic solvent for the extraction in step (c) is a solvent selected from the group consisting of ethanol, methanol, and acetone.

4. The method according to claim 3, wherein said organic solvent is ethanol.

5. The method according to claim 1, wherein said method further comprises the steps of:
   f. mixing said flour obtained in step (b) with said organic solvent to obtain a mixture;
   g. heating said mixture obtained in step (f); and
   h. filtering said heated mixture in step (g) to remove undissolved particles to obtain said organic solvent extract of isoflavones.

6. The method according to claim 5 wherein said mixing of solvent and flour in step (f) is conducted at a solvent:flour ratio of 1:1 to 10:1 (mL:g).

7. The method according to claim 5 wherein said heating in step (g) is conducted at a temperature in the range of 40-90° C. for at least 2 hours.

8. The method according to claim 5 wherein said method further comprises the steps of:
   i. mixing said organic solvent extract obtained in step (c) with acid to adjust the pH of the resulting mixture to 1-5; and
   j. heating said mixture obtained in step (i) at a temperature in the range of 40-90° C. for at least 1 hour and obtaining said hydrolysate.

9. The method according to claim 1 wherein said acid for the hydrolysis in step (d) is hydrochloric acid or acetic acid.

10. The method according to claim 9, wherein said hydrochloric acid is 37%.

11. The method according to claim 8 wherein said method further comprises the steps of:
    k. mixing said hydrolysate obtained in step (d) with water to obtain said aqueous mixture;
    l. cooling said aqueous mixture obtained in step (k) to room temperature or below for at least 10 minutes and precipitating said isoflavone aglycone crystals therefrom;
    m. filtering said cooled aqueous mixture obtained in step (l) to obtain said isoflavone aglycone crystals; and
    n. collecting and drying said isoflavone aglycone crystals obtained in step (m) to form an isoflavone aglycone product.

12. The method according to claim 11, wherein said mixing of hydrolysate in step (k) is conducted at a ratio of 1:1 to 15:1 (mL:mL).

13. The method according to claim 11 further comprising the steps of:
    o. washing said isoflavone aglycone crystals obtained in step (e) with a solvent;
    p. re-dissolving said washed product obtained in step (o) in a solvent;
    q. re-crystallizing said re-dissolved product obtained in step (p) by adding water into said re-dissolved product to form second crystals; and
    collecting and drying said second crystals obtained in step (q) to form a purified isoflavone aglycone product.

14. The method according to claim 13, wherein said solvent for washing in step (o) is water; wherein said solvent for re-dissolving in step (p) is 95- 99.99% ethanol.

15. The method according to claim 1 wherein said hydrolysis step (d) is conducted after said extraction step (c).

16. The method according to claim 1 wherein the volume of said aqueous mixture increases by 4 to 15 times upon addition of water into said hydrolysate in the crystallization step (e).

17. The method according to claim 5, wherein said filtration step is conducted in the absence of ultrafiltration.

* * * * *